Figure 1:
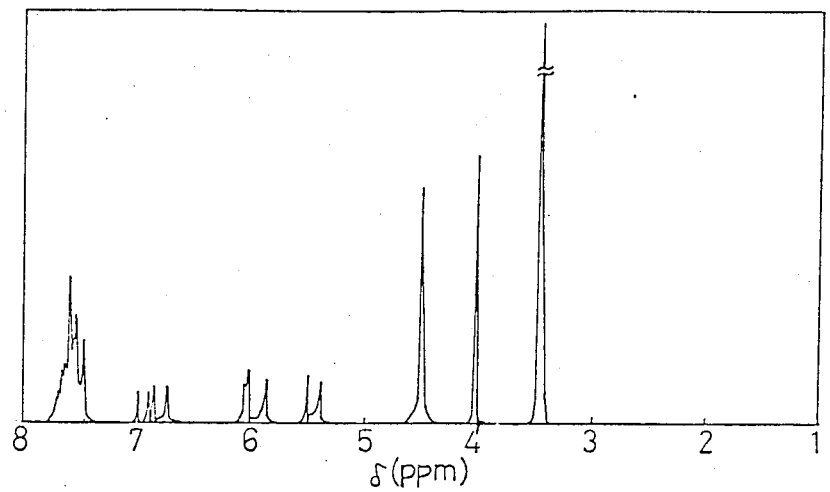

United States Patent [19]

Ishikura et al.

[11] Patent Number: 4,543,216
[45] Date of Patent: Sep. 24, 1985

[54] POLYMERIZABLE AMINO ACID COMPOUNDS AND THEIR PRODUCTION

[75] Inventors: Shinichi Ishikura, Kyoto; Tamotsu Yoshioka, Osaka; Ryuzo Mizuguchi, Kyoto, all of Japan

[73] Assignee: Nippon Paint Co., Ltd., Osaka, Japan

[21] Appl. No.: 594,826

[22] Filed: Mar. 29, 1984

Related U.S. Application Data

[60] Division of Ser. No. 372,729, Apr. 28, 1982, Pat. No. 4,452,746, which is a continuation-in-part of Ser. No. 253,143, Apr. 10, 1981, abandoned.

[30] Foreign Application Priority Data

Apr. 10, 1980 [JP] Japan .................................. 55-47651
Apr. 10, 1980 [JP] Japan .................................. 55-47652

[51] Int. Cl.$^4$ ........................................... C07C 143/68
[52] U.S. Cl. ................................. 260/501.12; 544/158
[58] Field of Search ....................... 260/501.12; 544/158

[56] References Cited

PUBLICATIONS

Belyaeu et al., *Chemical Abstracts*, vol. 76, #85542v, "2-Phenylallylmercaptan", 10/19/1972.

*Primary Examiner*—Glennon H. Hollrah
*Assistant Examiner*—Raymond Covington
*Attorney, Agent, or Firm*—Wenderoth, Lind & Ponack

[57] ABSTRACT

A polymerizable amino acid compound of the formula:

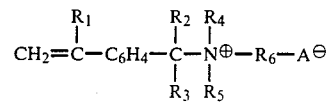

wherein $R_1$, $R_2$ and $R_3$ are each hydrogen or methyl, $R_4$ is $C_1$-$C_{20}$ alkyl optionally bearing at least one hydroxyl and optionally having —O— or —COO— in the alkyl chain, $R_5$ is hydrogen or $C_1$-$C_{20}$ alkyl optionally bearing at least one hydroxyl and optionally having —O— or —COO— in the alkyl chain, or when $R_4$ and $R_5$ are taken together with the nitrogen atom to which they are attached, they represent a nitrogen atom containing heterocyclic group, $R_6$ is an alkylene group having not more than 6 carbon atoms and A is —COO— or —SO$_3$—, provided that when $R_4$ is $C_1$-$C_{20}$ alkyl, $R_5$ is not hydrogen, which is highly soluble in water or organic solvents without any acidic or basic substance and can be introduced into the molecule of high molecular compounds.

5 Claims, 13 Drawing Figures

POLYMERIZABLE AMINO ACID COMPOUNDS AND THEIR PRODUCTION

This is a division of Ser. No. 372,729 now U.S. 4,452,746, filed Apr. 28, 1982 which is a continuation in part of Ser. No. 253,143, filed Apr. 10, 1981, now abandoned.

The present invention relates to polymerizable amino acid compounds and their production. More particularly, it relates to polymerizable amino acid compounds which can be introduced into the molecule of high molecular compounds so as to modify their physical and chemical properties, and their production.

When an ionic functional group is introduced into a high molecular compound, the physical and chemical properties of the high molecular compound are greatly modified even if the introduced amount of the ionic functional group is small. Further, the characteristic properties of an ionic functional group are emphasized when the ionic functional group is introduced into a high molecular compound. Because of these reasons, the study on high molecular compounds having ionic functional groups has been highly developed. An interest towards polymerizable monomers having an inner salt structure and their introduction into high molecular compounds for enhancing advantageously the reactivity, surface activity, electrochemical properties, biological properties, etc. is particularly increased. For instance, Japanese Patent Publication (examined) No. 11651/1967. discloses the compound of the formula:

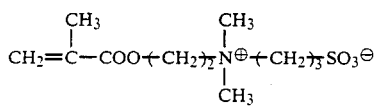

Further, for instance, U.S. Pat. No. 2,840,603 discloses the compounds of the formula:

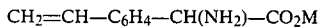

wherein M is a cation such as hydrogen, ammonium or metal.

In general, ampho-ionic compounds are known to show a lower solubility at an isoelectric point. Accordingly, it is necessary to enhance their solubility by the use of an acidic or basic substance for employing them in the form of solution. However, the use of such acidic or basic substance produces the following problems:

(1) When an acidic or basic substance is added to enhance the solubility of an ampho-ionic compound, the opposite pH condition can not be adopted so that the separation of the zwitter monomer sometimes takes place and the polymerization therewith hardly proceeds. Further, the scopes of the initiator and other additives to be usable on the polymerization are quite restricted.

(2) The polymer composition obtained by polymerization in the presence of an acidic or basic substance has more or less a tendency to lower the dispersibility of a pigment therein and reduce the performances of a coating film formed thereon in comparison with the polymer composition obtained by polymerization in the absence of an acidic or basic substance.

The main object of the present invention is to provide novel compounds which have an inner salt structure and are soluble in water, organic solvents or liquid monomers, etc. and also which are usable as polymerizable monomers imparting their characteristic properties to high molecular compounds.

The novel compounds which are suitable for the said object and can be provided by this invention are polymerizable amino acid compounds having an ionic functional group and a carboxylic or sulfonic acid residue as well as a polymerizable C—C double bond. Such polymerizable amino acid compounds are representable by the formula:

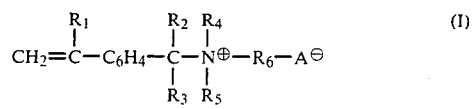

wherein $R_1$, $R_2$ and $R_3$ are each hydrogen or methyl, $R_4$ is $C_1$-$C_{20}$ and alkyl optionally bearing at least one hydroxyl and optionally having —O— or —COO— in the alkyl chain, $R_5$ is hydrogen or $C_1$-$C_{20}$ alkyl optionally bearing at least one hydroxyl and optionally having —O— or —COO— in the alkyl chain, or when $R_4$ and $R_5$ are taken together with the nitrogen atom to which they are attached, they represent a nitrogen atom containing heterocyclic group, $R_6$ is an alkylen group having not more than 6 carbon atoms and A is —COO— or —$SO_3$—, provided that when $R_4$ is $C_1$-$C_{20}$ alkyl, $R_5$ is not hydrogen. The group of —$C_6H_4$— represents a benzene ring throughout the specification.

The polymerizable amino acid compound (I) can be produced by reacting a benzyl halide compound with an amino acid compound. The reaction is preferably carried out under a basic condition. A typical procedure comprises reacting a benzyl halide compound with an amino acid compound in the presence of a basic substance (e.g. alkali metal hydroxides, alkali metal alkoxides, ammonia, organic amines) in a solvent such as alcohols, ethylene glycol monoalkyl ethers, dimethylformamide, dimethylsulfoxide or water, or their mixtures at a temperature of 0° to 150° C. under an atmospheric or elevated pressure for a period of 10 minutes to 48 hours, usually while stirring.

As the benzyl halide compound, there may be employed the one representable by the formula:

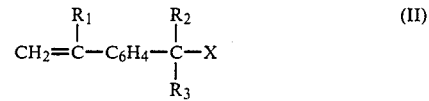

wherein X is chlorine or bromine and $R_1$, $R_2$ and $R_3$ are each as defined above. Specific examples are vinylbenzyl chloride, vinylbenzyl bromide, isopropenylbenzyl chloride, isopropenylbenzyl bromide, etc. Among them, the most usually available is vinylbenzyl chloride. Commercially, they are available as a mixture of isomers on the benzene ring such as a mixture of m- and p-isomers and may be as such employed as the starting material without separation into each isomer. The resulting product in such case is also a mixture of isomers on the benzene ring.

As the amino acid compound, there may be employed the one representable by the formula:

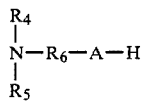 (III)

wherein $R_4$, $R_5$, $R_6$ and A are each as defined above. Specific examples are N,N-dimethylglycine, N,N-diethylglycine, N-methyl-N-dodecylglycine, N,N-dimethylalanine, N,N-diethylalanine, N-methyl-N-dodecylalanine, N,N-dimethyl-β-alanine, N,N-diethyl-β-alanine, N-methyl-N-dodecyl-β-alanine, N,N-dimethyl-ε-aminocaproic acid, N,N-diethyl-ε-aminocaproic acid, N-methyl-N-dodecyl-ε-aminocaproic acid, N,N-dimethyltaurine, N,N-diethyltaurine, N-methyl-N-dodecyltaurine, N-carboxymethyl-pyrrolidone, N-carboxymethyl-piperidine, N-carboxymethyl-morpholine, N-(1-carboxyethyl)-pyrrolidone, N-(1-carboxyethyl)-piperidine, N-(1-carboxyethyl)-morpholine, N-(2-carboxyethyl)-pyrrolidone, N-(2-carboxyethyl)-piperidine N-(2-carboxyethyl)-morpholine, N-(5-carboxypentyl)-pyrrolidone, N-(5-carboxypentyl)-piperidine, N-(5-carboxypentyl)-morpholine, 2-pyrrolidinoethane-suulfonic acid-(1), 2-piperidinoethane-sulfonic acid-(1), 2-morpholinoethane-sulfonic acid-(1), N-hydroxymethylglycine, N-hydroxyethylglycine, N,N-bis(hydroxyethyl)glycine, N-[2-hydroxy-1,1-bis(hydroxymethyl)]-ethylglycine, N-hydroxyethyl-N-dodecylglycine, N-hydroxymethylalanine, N-hydroxyethylalanine, N,N-bis(hydroxyethyl)]alanine, N-[2-hydroxy-1,1-bis(hydroxymethyl)]ethylalanine, N-hydroxyethyl-N-dodecylalanine, N-hydroxymethyl-β-alanine, N-hydroxyethyl-β-alanine, N,N-bis(hydroxyethyl)-β-alanine, N-[2-hydroxy-1,1-bis(hydroxymethyl)]ethyl-β-alanine, N-hydroxyethyl-N-dodecyl-β-alanine, N-hydroxymethyl-ε-aminohexanoic acid, N-hydroxyethyl-ε-aminohexanoic acid, N,N-bis(hydroxyethyl)-ε-aminohexanoic acid, N-[2-hydroxy-1,1-bis(hydroxymethyl)]ethyl-ε-aminohexanoic acid, N-hydroxyethyl-N-dodecyl-ε-aminohexanoic acid, N-hydroxymethyltaurine, N-hydroxyethyltaurine, N,N-bis(hydroxyethyl)taurine, N-[2-hydroxy-1,1-bis(hydroxymethyl)]ethyltaurine, N-hydroxyethyl-N-dodecyltaurine, etc.

Among these amino acid compounds, those of the formula:

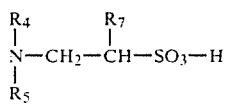 (III')

wherein $R_7$ is hydrogen or methyl and $R_4$ and $R_5$ are each as defined above may be produced by reacting an amine of the formula:

wherein $R_4$ and $R_5$ are each as defined above with a sulfonic salt of the formula:

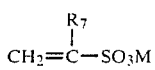

wherein M is an alkali metal and $R_7$ is as defined above, followed by treatment for elimination of the alkali metal.

Alternatively, the polymerizable amino acid compound (I) may be produced by reacting a benzylamine compound of the formula:

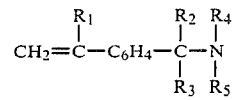 (IV)

wherein $R_1$, $R_2$, $R_3$, $R_4$ and $R_5$ are each as defined above with a haloacid or its ester of the formula:

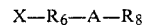 (V)

wherein $R_8$ is hydrogen or a $C_1$-$C_{12}$ hydrocarbon group, and $R_6$, X and A are each as defined above, optionally followed by hydrolysis in the presence of an alkaline catalyst. The main reaction may be carried out at a temperature of 0° to 150° C. under an ordinary or elevated pressure for a period of 10 minutes to 100 hours in the presence or absence of a solvent such as hydrocarbons, esters, ketones, alcohols, ethers, amides, nitriles or sulfoxides, and their mixtures usually while stirring. The subsequent hydrolysis may be effected in a per se conventional procedure.

Examples of the benzylamine compound (IV) are N,N-dimethyl-(vinylbenzyl)amine, N,N-dimethyl-(isopropenylbenzyl)amine, N,N-diethyl-(vinylbenzyl)amine, N,N-diethyl(isopropenylbenzyl)amine, N,N-dioctyl-(vinylbenzyl)amine, N,N-dioctyl-(isopropenylbenzyl)amine, N-methyl-N-ethyl(vinylbenzyl)amine, N-methyl-N-ethyl-(isopropenylbenzyl)amine, N-methyl-N-dodecyl-(vinylbenzyl)amine, N-methyl-N-dodecyl-(isopropenylbenzyl)amine, N-hydroxymethyl-(vinylbenzyl)amine, N-hydroxymethyl-(isopropenylbenzyl)amine, N-hydroxymethyl(vinylbenzyl)amine, N-hydroxyethyl-(isopropenylbenzyl)amine, N,N-bis(hydroxyethyl)-(vinylbenzyl)amine, N,N-bis(hydroxyethyl)-(isopropenylbenzyl)amine, N-[2-hydroxy-1,1-bis(hydroxymethyl)]-ethyl-N-(vinylbenzyl)amine, N-[2-hydroxy-1,1-bis(hydroxymethyl)]ethyl-N-(isopropenylbenzyl)amine, N-hydroxyethyl-N-(vinylbenzyl)dodecylamine, etc.

Examples of the haloacid or its esters (V) are chloroacetic acid, bromoacetic acid, ethyl chloroacetate, 2-chloropropionic acid, 2-bromopropionic acid, 5-chloro-ε-caproic acid, 5-bromo-ε-caproic acid, etc.

Alternatively, the polymerizable amino acid compound of the formula:

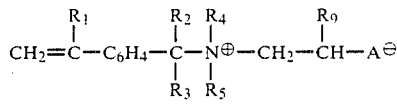 (I')

wherein $R_9$ is hydrogen or methyl and $R_1$, $R_2$, $R_3$, $R_4$, $R_5$ and A are each as defined above may be produced by reacting the benzylamine compound (IV) with an α,β-unsaturated acid or its ester of the formula:

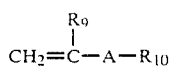 (VI)

wherein $R_{10}$ is hydrogen or a $C_1$-$C_{12}$ hydrocarbon group, optionally followed by hydrolysis of the addition product in the presence of an alkaline catalyst. The main reaction, i.e. addition, may be carried out, if necessary, in the presence of a solvent such as alcohols, ethylene glycol monoalkyl ethers, dimethylformamide, dimethylsulfoxide or water, or their mixture at a temperature of 0° to 150° C. under an atmospheric or elevated pressure for a period of 10 minutes to 48 hours. Examples of the α,β-unsaturated acid or its ester (VI) are vinylsulfonic acid, vinylcarboxylic acid, methyl vinylsulfonate, ethyl vinylsulfonate, n-butyl vinylsulfonate, 2-ethylhexyl vinylsulfonate, dodecyl vinylsulfonate, methyl acrylate, methyl methacrylate, ethyl acrylate, ethyl methacrylate, butyl acrylate, butyl methacrylate, dodecyl acrylate, dodecyl methacrylate, etc. In the case using the α,β-unsaturated acid (VI), it may be subjected to the reaction in its salt form such as alkali metal salt, ammonium salt or organic amine salt.

Examples of the produced polymerizable amino acid compound (I) are N,N-dimethyl-N-(vinylbenzyl)ammonioacetic acid betaine, N,N-dimethyl-N-(isopropenylbenzyl)ammonioacetic acid betaine, N,N-diethyl-N-(vinylbenzyl)ammonioacetic acid betaine, N,N-diethyl-N-(isopropenylbenzyl)-ammonioacetic acid betaine, N,N-octyl-N-(vinylbenzyl)-ammonioacetic acid betaine, N,N-dioctyl-N-(isopropenylbenzyl)-ammonioacetic acid betaine, N-methyl-N-dodecyl-N-(vinylbenzyl)ammonioacetic acid betaine, N-methyl-N-dodecyl-N-(isopropenylbenzyl)ammonioacetic acid betaine, N,N-dimethyl-N-(vinylbenzyl)ammoniopropionic acid-1 betaine, N-N-dimethyl-N-(isopropenylbenzyl)ammoniopropionic acid-1betaine, N,N-diethyl-N-(vinylbenzyl)ammoniopropionic acid-1 betaine, N,N-diethyl-N-(isopropenylbenzyl)ammniopropionic acid-1 betaine, N,N-dioctyl-N-(vinylbenzyl)ammoniopropionic acid-1 betaine, N,N-dioctyl-N-(isopropenylbenzyl)ammoniopropionic acid-1 betaine, N-methyl-N-dodecyl-N-dodecyl-N-(vinylbenzyl)ammoniopropionic acid-1 betaine, N-methyl-N-dodecyl-N-(isopropenylbenzyl)-ammoniopropionic acid-1 betaine, N,N-dimethyl-N-(vinylbenzyl)ammoniopropionic acid-2 betaine, N,N-dimethyl-N-(isopropenylbenzyl)ammoniopropionic acid-2 betaine, N,N-diethyl-N-(vinylbenzyl)ammonioacetic acid betaine, N,N-diethyl-N-(isopropenylbenzyl)ammoniopropionic acid-2 betaine, N,N-dioctyl-N-(vinylbenzyl)ammoniopropionic acid-2 betaine, N,N-dioctyl-N-(isopropenylbenzyl)ammoniopropionic acid-2 betaine, N-methyl-N-dodecyl-N-(vinylbenzyl)ammoniopropionic acid-2 betaine, N-methyl-N-dodecyl-N-(isopropenylbenzyl)ammoniopropionic acid-2 betaine, N,N-dimethyl-N-(vinylbenzyl)-ammoniocaproic acid-5 betaine, N,N-dimethyl-N-(isopropenylbenzyl)ammoniocaproic acid-5 betaine, N,N-diethyl-N-(vinylbenzyl)ammoniocaproic acid-5 betaine, N,N-diethyl-N-(isopropenylbenzyl)ammoniocaproic acid-5 betaine, N,N-dioctyl-N-(vinylbenzyl)ammoniocaproic acid-5 betaine, N,N-dioctyl-N-(isopropenylbenzyl)ammoniocaproic acid-5 betaine, N-methyl-N-dodecyl-N-(vinylbenzyl)ammoniocaproic acid-5 betaine, N-methyl-N-dodecyl-N-(isopropenylbenzyl)ammoniocaproic acid-5 betaine, N,N-dimethyl-N-(vinylbenzyl)ammonioethanesulfonic acid-2 betaine, N,N-dimethyl-N-(isopropenylbenzyl)ammonioethanesulfonic acid-2 betaine, N,N-diethyl-N-(vinylbenzyl)-ammonioethanesulfonic acid-2 betaine, N,N-diethyl-N-(isopropenylbenzyl)ammonioethanesulfonic acid-2 betaine, N,N-dioctyl-N-(vinylbenzyl)ammonioethanesulfonic acid-2 betaine, N,N-dioctyl-N-(isopropenylbenzyl)ammonioethanesulfonic acid-2 betaine, N-methyl-N-dodecyl-N-(vinylbenzyl)ammonioethanesulfonic acid-2 betaine, N-methyl-N-dodecyl-N-(isopropenylbenzyl)ammonioethanesulfonic acid-2 betaine, N-hydroxymethyl-N-(vinylbenzyl)glycine, N-hydroxymethyl-N-(isopropenylbenzyl)glycine, N-hydroxyethyl-N-(vinylbenzyl)glycine, N-hydroxyethyl-N-(isopropenylbenzyl)glycine, N,N-bis(hydroxyethyl)-N-(vinylbenzyl)ammonioacetic acid betaine, N,N-bis(hydroxyethyl)-N-(isopropenylbenzyl)ammonioacetic acid betaine, N-[2-hydroxy-1,1-bis(hydroxymethyl)]ethyl-N-(vinylbenzyl)-glycine, N-[2-hydroxy-1,1-bis(hydroxymethyl)]ethyl-N-(isopropenylbenzyl)glycine, N-hydroxyethyl-N-dodecyl-N-(vinylbenzyl)ammonioacetic acid betaine, N-hydroxyethyl-N-dodecyl-N-(isopropenylbenzyl)ammonioacetic acid betaine, N-hydroxymethyl-N-(vinylbenzyl)alanine, N-hydroxymethyl-N-(isopropenylbenzyl)alanine, N-hydroxyethyl-N-(vinylbenzyl)alanine, N-hydroxyethyl-N-(isopropenylbenzyl)alanine, N,N-bis(hydroxyethyl)-N-(vinylbenzyl)ammoniopropionic acid-1 betaine, N,N-bis(hydroxyethyl)-N-(isopropenylbenzyl)ammoniopropionic acid-1 betaine, N-[2-hydroxy-1,1-bis(hydroxymethyl)]ethyl-N-(vinylbenzyl)alanine, N-[2-hydroxy-1,1-bis(hydroxymethyl)]-ethyl-N-(isopropenylbenzyl)alanine, N-hydroxyethyl-N-dodecyl-N-(vinylbenzyl)ammoniopropionic acid-1 betaine, N-hydroxyethyl-N-dodecyl-N-(isopropenylbenzyl)ammoniopropionic acid-1 betaine, N-hydroxymethyl-N-(vinylbenzyl)-β-alanine, N-hydroxymethyl-N-(isopropenylbenzyl)-β-analine, N-hydroxyethyl-N-(vinylbenzyl)-β-alanine, N-hydroxyethyl-N-(isopropenylbenzyl)-β-alanine, N,N-bis(hydroxyethyl)-N-(vinylbenzyl)ammoniopropionic acid-2 betaine, N,N-bis(hydroxyethyl)-N-(isopropenylbenzyl)ammoniopropionic acid-2 betaine, N-[2-hydroxy-1,1-bis(hydroxymethyl)]ethyl-N-(vinylbenzyl)-β-alanine, N-]2-hydroxy-1,1-bis(hydroxymethyl)]ethyl-N-(isopropenylbenzyl)-β-alanine, N-hydroxyethyl-N-dodecyl-N-(vinylbenzyl)ammoniopropionic acid-2 betaine, N-hydroxyethyl-N-dodecyl-N-(isopropenylbenzyl)ammoniopropionic acid-2 betaine, N-hydroxymethyl-N-(vinylbenzyl)-ε-aminohexanoic acid, N-hydroxymethyl-N-(isopropenylbenzyl)-ε-aminohexanoic acid, N-hydroxyethyl-N-(vinylbenzyl)-ε-aminohexanoic acid, N-hydroxyethyl-N-(isopropenylbenzyl)-ε-aminohexanoic acid, N,N-bis(hydroxyethyl)-N-(vinylbenzyl)ammoniocaproic acid-5 betaine, N,N-bis(hydroxyethyl)-N-(isopropenylbenzyl)ammoniocaproic acid-5 betaine, N-[2-hydroxy-1,1-bis(hydroxymethyl)]-ethyl-N-(vinylbenzyl)-ε-aminohexanoic acid, N-[2-hydroxy-1,1-bis(hydroxymethyl)]ethyl-N-(isopropenylbenzyl)-ε-aminohexanoic acid, N-hydroxyethyl-N-dodecyl-N-(vinylbenzyl)ammoniocaproic acid-5 betaine, N-hydroxyethyl-N-dodecyl-N-(isopropenylbenzyl)ammoniocaproic acid-5 betaine, N-hydroxymethyl-N-(vinylbenzyl)taurine, N-hydroxymethyl-N-(isopropenylbenzyl)taurine, N-hydroxyethyl-N-(vinylbenzyl)taurine, N-hydroxyethyl-N-(isopropenylbenzyl)taurine, N,N-bis(hydroxyethyl)-N-(vinylbenzyl)ammonioethanesulfonic acid-2 betaine, N,N-bis(hydroxyethyl)-N-(isopropenylbenzyl)ammonioethanesulfonic acid-2 betaine, N-[2-hydroxy-1,1-bis(hydroxymethyl)]-ethyl-N-(vinylbenzyl)taurine, N-[2-hydroxy-1,1-bis(hydroxymethyl)]ethyl-N-(isopropenylbenzyl)taurine, N-hydroxyethyl-N-dodecyl-N-(vinylbenzyl)ammonioethanesulfonic acid-2 betaine, N-hydroxyethyl-N-dodecyl-N-(isopropenylbenzyl)ammonioethanesulfonic acid-2 betaine, etc.

The polymerizable amino acid compounds (I) have advantageous reactivity, surface activity, electrochemical properties, biological properties, etc. They are highly soluble in water or organic solvents without any acidic or basic substance and can be introduced into high molecular substances with imparting zwitter characteristics thereto. Particularly, the polymerizable amino acid compounds (I) wherein the acidic group represented by the symbol A is a sulfonium group behave as strongly acidic inner salt compounds. When the polymerizable amino acid compounds (I) are copolymerized with other polymerizable monomers, there can be obtained resins for dispersing pigments therein. Such copolymerization may be carried out by per se conventional polymerization procedures such as radical polymerization, radiation polymerization, cationic polymerization and anionic polymerization. Examples of the other polymerizable monomers are acrylic monomers, styrenic monomers, conjugated diene monomers, vinyl acetate, ethylene, propylene, vinyl chloride, etc.

Practical and presently preferred embodiments of the present invention are illustratively shown in the following Examples wherein part(s) are by weight.

EXAMPLE 1

Into a 2 liter volume flask equipped with a stirrer, a thermometer and a cooler, N,N-dimethyl-(vinylbenzl)amine (161 parts), dimethylformamide (700 parts) and ethyl chloroacetate (122 parts) are charged, and the resultant mixture is heated at 60° C. under stirring. Triethylamine (101 parts) is dropwise added thereto, and stirring is continued at 70° C. for 2 hours. After separation of triethylamine hydrochloride as precipitated by filtration, the mother liquor is added to a solution of sodium hydroxide (40 parts) in water (300 parts) at 100° C. for hydrolysis. The reaction mixture is neutralized with hydrochloric acid, and acetone is added thereto. The precipitated substance is collected by filtration and dried under reduced pressure to give a white solid material (203 parts), of which the NMR chart is as shown in FIG. 1 of the accompanying drawings. Thus, the product is identified to be N,N-dimethyl-N-(vinylbenzyl)ammonioacetic acid betaine of the formula:

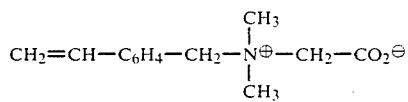

EXAMPLE 2

Figure 2:
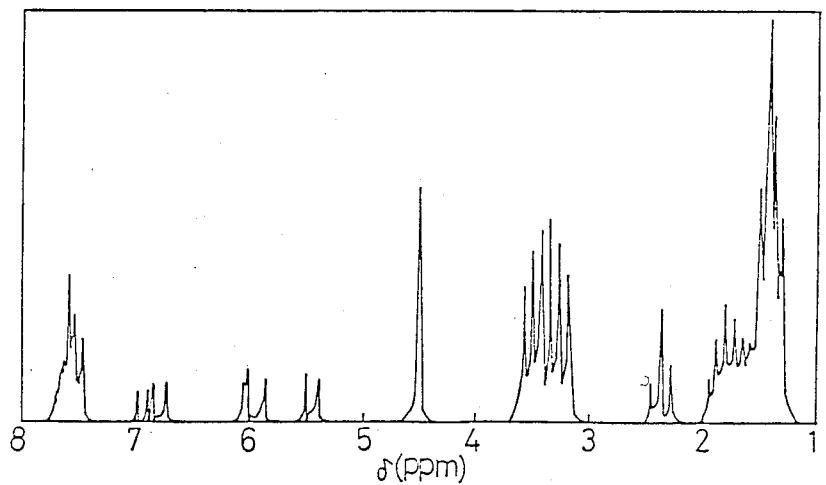

Into the same flask as in Example 1, N,N-diethyl-ε-aminocaproic acid (182 parts), sodium hydroxide (40 parts), deionized water (300 parts) and ethylene glycol monoethyl ether (150 parts) are charged, and the resultant mixture is heated at 80° C. under stirring. A mixture of vinylbenzyl chloride (153 parts) and ethylene glycol monomethyl ether (100 parts) is dropwise added thereto in 2 hours, during which sodium hydroxide (each 20 parts) is added thereto 1 hour and 2 hours after the start of the dropwise addition. Stirring under heating is further continued for 10 hours. The reaction mixture is neutralized with hydrochloric acid, and acetone is added thereto to precipitate a white solid substance. The white solid substance is collected by filtration and dried under reduced pressure to give N,N-diethyl-N-(vinylbenzyl)ammoniocaproic acid-5 betaine (238 parts) of the formula:

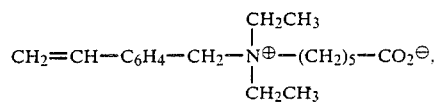

of which the NMR chart is shown in FIG. 2.

EXAMPLE 3

Figure 3:
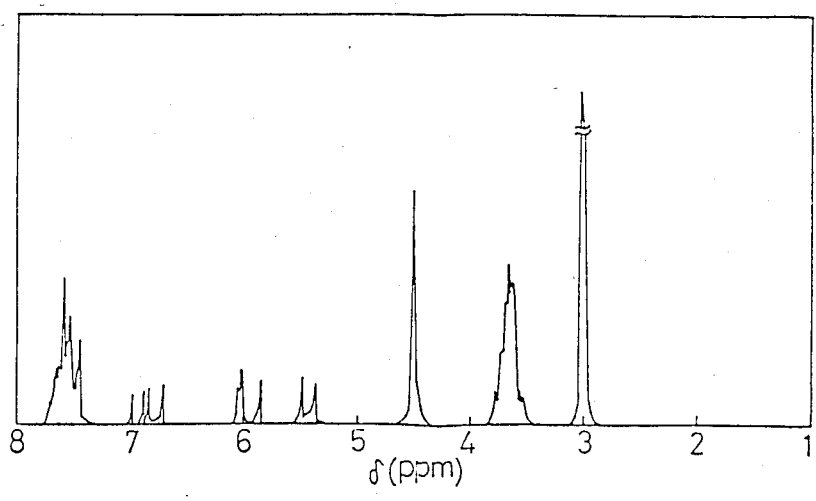

Into the same flask as in Example 1, N,N-dimethyltaurine (153 parts), ethylene glycol (250 parts), sodium ethylate (68 parts) and ethylene glycol monomethyl ether (100 parts) are charged, and the resultant mixture is heated to 100° C. under stirring. A mixture of vinylbenzyl chloride (153 parts) and ethylene glycol monomethyl ether (100 parts) is dropwise added thereto in 2 hours, and stirring is continued for 5 hours. Acetone is added to the reaction mixture to precipitate a white solid substance. The substance is collected by filtration and dried under reduced pressure to give N,N-dimethyl-N-(vinylbenzyl)ammonioethanesulfonic acid-2 betaine (220 parts) of the formula:

$$CH_2=CH-C_6H_4-CH_2-\overset{CH_3}{\underset{CH_3}{N^\oplus}}-CH_2CH_2-SO_3^\ominus,$$

of which the NMR chart is shown in FIG. 3.

EXAMPLE 4

Figure 4:
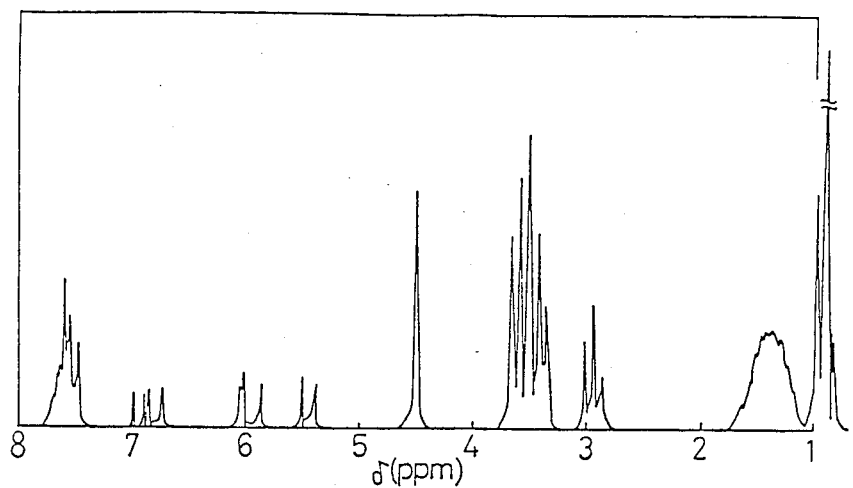

In the same manner as in Example 3 but using N,N-di-n-butyl-β-alanine in place of N,N-dimethyltaurine, the reaction is carried out to give N,N-di-n-butyl-N-(vinylbenzyl)ammoniopropionic acid-2 betaine (256 parts) of the formula:

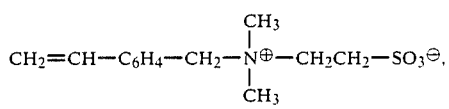

of which the NMR chart is shown in FIG. 4.

EXAMPLE 5

Figure 5:
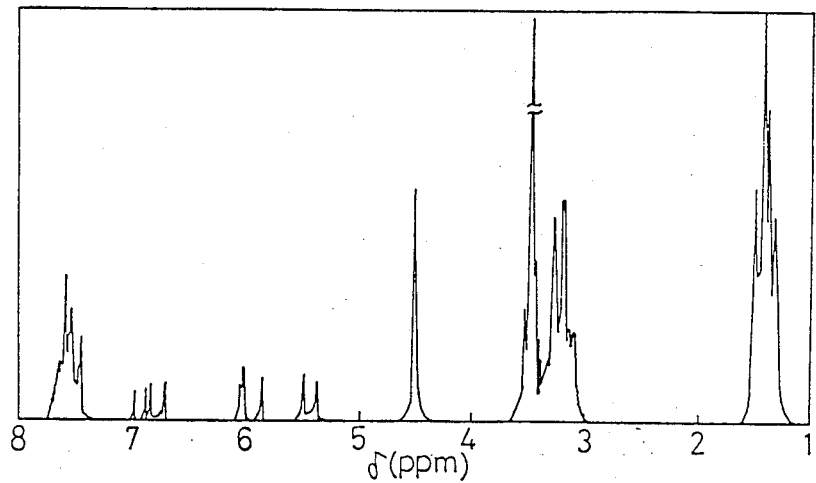

In the same manner as in Example 3 but using N,N-diethyltaurine (181 parts), the reaction is carried out to give N,N-diethyl-N-(vinylbenzyl)ammonioethanesulfonic acid-2 betaine (242 parts) of the formula:

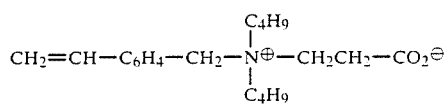

of which the NMR chart is shown in FIG. 5.

EXAMPLE 6

Figure 6:
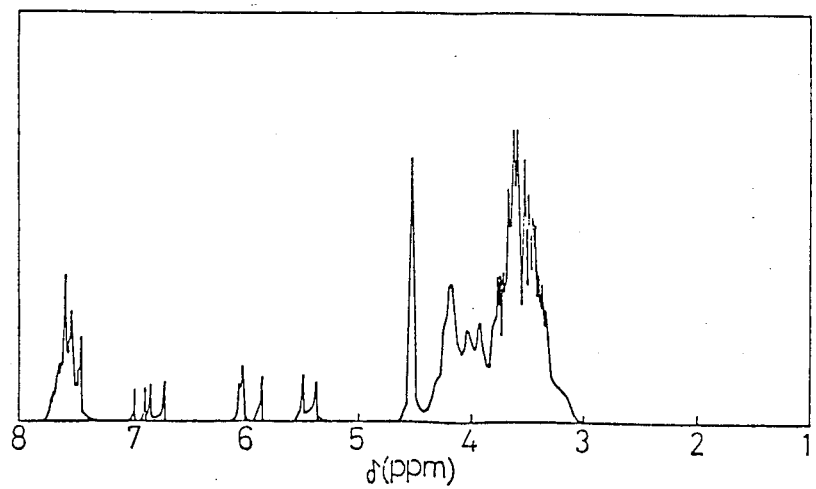

In the same manner as in Example 3 but using N-(2-sulfoethyl)morpholine (195 parts), the reaction is carried out to give N-(vinylbenzyl)morpholinoethanesulfonic acid-2 betaine (250 parts) of the formula:

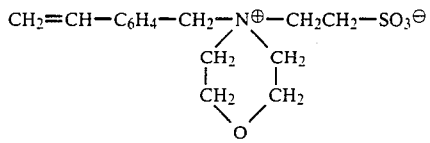

of which the NMR chart is shown in FIG. 6.

EXAMPLE 7

Figure 7:
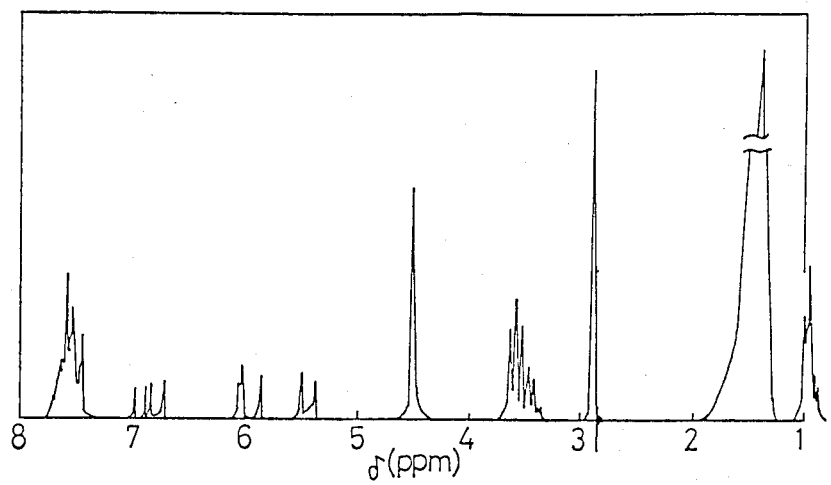

In the same manner as in Example 3 but using N-methyl-N-(n-dodecyl)taurine (277 parts), the reaction is carried out to give N-methyl-N-(n-dodecyl)-N-(vinylbenzyl)-ammonioethanesulfonic acid-2 betaine (312 parts) of the formula:

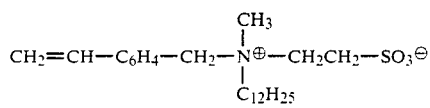

of which the NMR chart is shown in FIG. 7.

Reference Examples

Solubilities of the compounds obtained in Examples 1 to 7 in water at 20° C. or 80° C. or in methanol at 30° C. are shown in Table 1 in terms of amount (g) of the compound soluble in 100 g of solvent. For comparison, solubilities of N-(vinylbenzyl)glycine (Comparative Example 1), N-(vinylbenzyl)-$\beta$-alanine (Comparative Example 2), N-(vinylbenzyl)-taurine (Comparative Example 3) and N-methyl-N-(vinylbenzyl)-taurine (Comparative Example 4) in the same solvents are shown in Table 1.

TABLE 1

| Compound | Solubility in water (g) | | Solubility in methanol (g) |
|---|---|---|---|
| | 20° C. | 80° C. | 30° C. |
| Example | | | |
| 1 | >100 | >100 | 1–20 |
| 2 | 20–100 | >100 | 20–100 |
| 3 | >100 | >100 | 1–20 |
| 4 | 20–100 | >100 | 20–100 |
| 5 | >100 | >100 | 1–20 |
| 6 | >100 | >100 | 20–100 |
| 7 | 1–20 | 20–100 | 1–20 |
| Comparative Example | | | |
| 1 | 0–1 | 0–1 | 0–1 |
| 2 | 0–1 | 0–1 | 0–1 |
| 3 | 0–1 | 0–1 | 0–1 |
| 4 | 0–1 | 0–1 | 0–1 |

EXAMPLE 8

In the same flask as in Example 1, N-(2-hydroxyethyl)-N-octyl-$\epsilon$-aminohexanoic acid (287 parts), water (300 parts), ethylene glycol monomethyl ether (200 parts) and sodium hydroxide (40 parts) are charged, and the resultant mixture is heated to 80° C. under stirring. After a homogeneous solution is attained, a mixture of vinylbenzyl chloride (153 parts) and ethylene glycol monomethyl ether (100 parts) is dropwise added thereto in 2 hours, during which sodium hydroxide (each 20 parts) is added thereto 1 hour and 2 hours after start of the dropwise addition. Stirring under heating is further continued for 6 hours. The reaction mixture is neutralized with dilute hydrochloric acid and acetone is added thereto to precipitate a white honey-like substance. The precipitated substance is dissolved in warm water and cooled. Then acetone is added thereto to reprecipitate the substance, which is dried under reduced pressure to give a white viscous material (304 parts). By NMR analysis, the material is identified to be N-(2-hydroxyethyl)-N-octyl-N-(vinylbenzyl)ammoniocaproic acid-5 betaine of the formula:

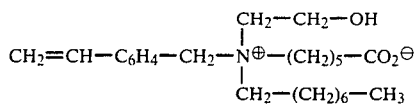

EXAMPLE 9

Into the same flask as in Example 1, N-[2-hydroxy-1,1-bis(hydroxymethyl)]ethyl-N-(isopropenylbenzyl)amine (251 parts), dimethylformaldehyde (1000 parts) and ethyl chloroacetate (125 parts) are charged, and the resultant mixture is heated at 60° C. under stirring. Triethylamine (101 parts) is dropwise added thereto, and stirring is continued at 70° C. for 2 hours. After separation of triethylamine hydrochloride as precipitated by filtration, the mother liquor is added to a solution of sodium hydroxide (40 parts) in water (300 parts) at 100° C. for hydrolysis. The reaction mixture is neutralized with hydrochloric acid, and acetone is added thereto to precipitate a substance, which is collected by filtration and dried under reduced pressure to give a white solid material (310 parts). By NMR, elementary analyses and measurement of molecular weight, the product is identified to be N-[2-hydroxy-1,1-bis(hydroxymethyl)]ethyl-N-(isopropenylbenzyl)glycine of the formula:

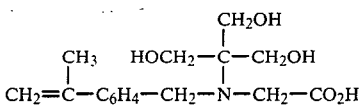

EXAMPLE 10

Figure 8:
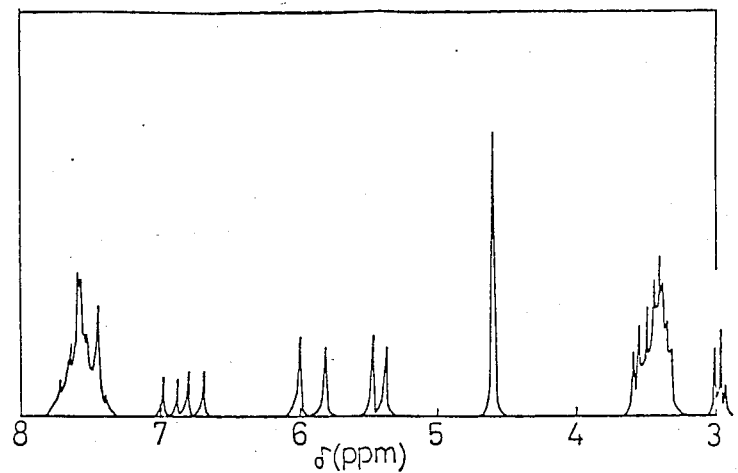

Into the same flask as in Example 1, N-(2-hydroxyethyl)-$\beta$-alanine (117 parts), sodium ethylate (68 parts), ethylene glycol (300 parts) and ethylene glycol monomethyl ether (150 parts) are charged, and the resultant mixture is heated at 100° C. under stirring. A mixture of vinylbenzyl chloride (152 parts) and ethylene glycol monomethyl ether (100 parts) is dropwise added thereto in 2 hours. Stirring under heating is further continued for 6 hours. The reaction mixture is neutralized with hydrochloric acid, and acetone is added thereto to precipitate a white solid substance. The white solid substance is collected by filtration and dried under reduced pressure to give N-(2-hydroxyethyl)-N-(vinylbenzyl)-$\beta$-alanine (191 parts) of the formula:

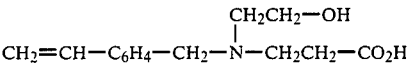

of which the NMR chart is shown in FIG. 8.

EXAMPLE 11

In the same flask as in Example 1, (hydroxyethyl)-(vinylbenzyl)amine (177 parts) and ethyl acrylate (100 parts) are charged, and the resultant mixture is heated at 80° C. for 3 hours while stirring. After addition of deionized water (200 parts) and sodium hydroxide (40 parts), the reaction mixture is subjected to hydrolysis at 100° C., followed by neutralization with hydrochloric acid. The precipitate is collected by filtration and dried under reduced pressure to give a white solid material (204 parts), of which the structure is identical with that of Example 10.

EXAMPLE 12

Figure 9:
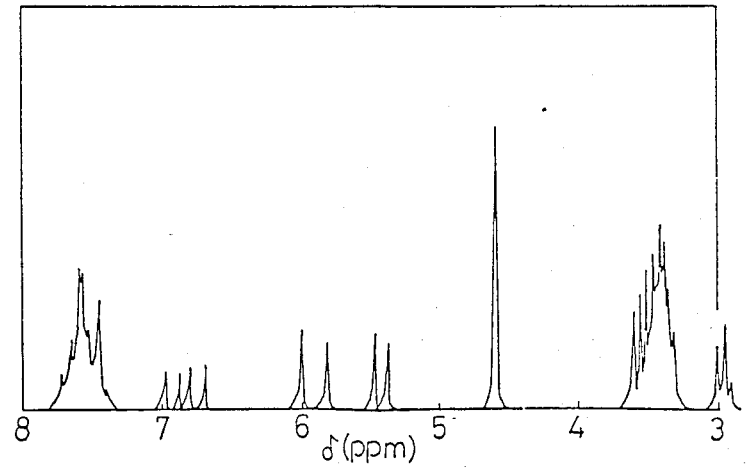

In the same manner as in Example 10 but using N,N-bis(2-hydroxyethyl)-β-alanine (161 parts) in place of N-(2-hydroxyethyl)-β-alanine, the reaction is carried out to give N,N-bis(2-hydroxyethyl)-N-(vinylbenzyl)ammoniopropionic acid-2 betaine (220 parts) of the formula:

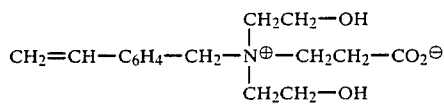

of which the NMR chart is shown in FIG. 9.

EXAMPLE 13

Figure 10:
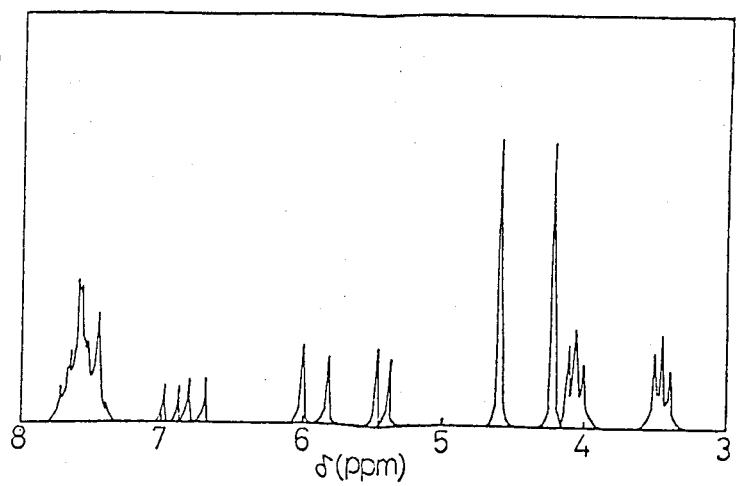

In the same manner as in Example 10 but using N-(2-hydroxyethyl)glycine (103 parts), the reaction is carried out to give N-(2-hydroxyethyl)-N-(vinylbenzyl)glycine (180 parts) of the formula:

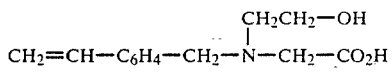

of which the NMR chart is shown in FIG. 10.

EXAMPLE 14

Figure 11:
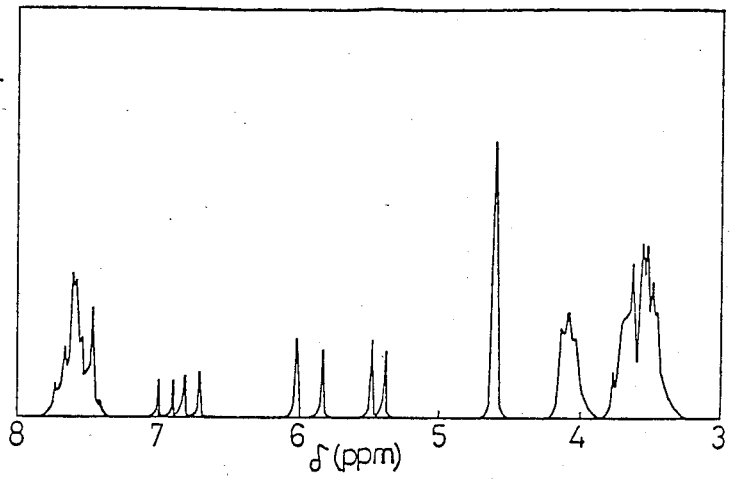

In the same manner as in Example 10 but using N-(2-hydroxyethyl)taurine (169 parts), the reaction is carried out to give N-(2-hydroxyethyl)-N-(vinylbenzyl)taurine (229 parts) of the formula:

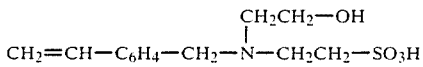

of which the NMR chart is shown in FIG. 11.

EXAMPLE 15

Figure 12:
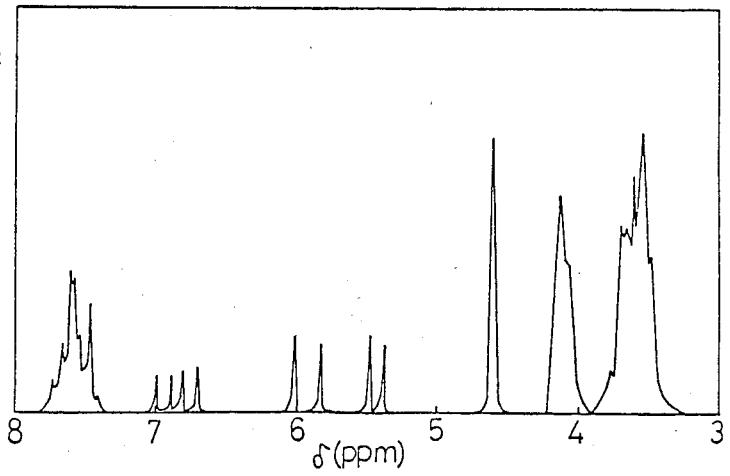

In the same manner as in Example 10 but using N,N-bis(2-hydroxyethyl)taurine (203 parts), the reaction is carried out to give N,N-bis(2-hydroxyethyl)-N-(vinylbenzyl)-ammonioethanesulfonic acid-2 betaine (263 parts) of the formula:

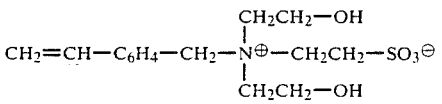

of which the NMR chart is shown in FIG. 12.

EXAMPLE 16

In the same manner as in Example 10 but using N-(2-hydroxydodecyl)taurine (309 parts), the reaction is carried out to give N-(2-hydroxydodecyl)-N-(vinylbenzyl)-taurine (327 parts) of the formula:

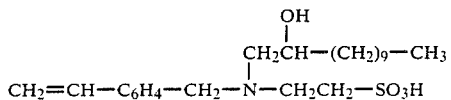

EXAMPLE 17

Figure 13:
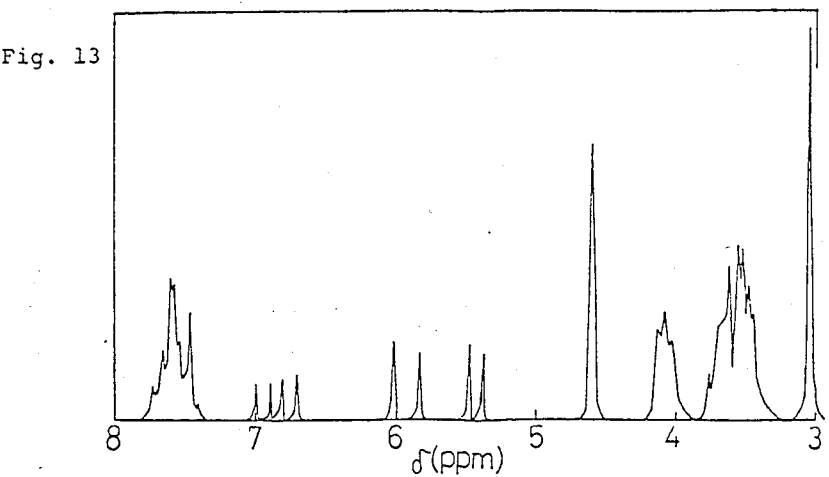

In the same manner as in Example 10 but using N-methyl-N-(2-hydroxyethyl)taurine (183 parts), the reaction is carried out to give N-methyl-N-(2-hydroxyethyl)-N-(vinylbenzyl)ammonioethanesulfonic acid-2 betaine (245 parts) of the formula:

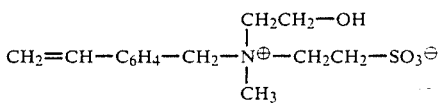

of which the NMR chart is shown in FIG. 13.

Reference Examples

Solubilities of the compounds obtained in Examples 8 to 17 in water at 20° C. or 80° C. are shown in Table 2 in terms of amount (g) of the compound soluble in 100 g of water. For comparison, solubilities of N-(vinylbenzyl)-glycine (Comparative Example 5), N-(vinylbenzyl)-β-alanine (Comparative Example 6), N-(vinylbenzyl)taurine (Comparative Example 7) and N-methyl-N-(vinylbenzyl)taurine (Comparative Example 8) in water are shown in Table 2.

| Compound | Solubility in water (g) | |
| --- | --- | --- |
| | 20° C. | 80° C. |
| Example | | |
| 8 | 1 | 10 |
| 9 | 4 | 60 |
| 10 | 1 | 20 |
| 11 | 1 | 20 |
| 12 | 2 | 30 |
| 13 | 2 | 30 |
| 14 | 1 | 20 |
| 15 | 2 | 25 |
| 16 | 1 | 10 |
| 17 | 6 | 100 |
| Comparative Example | | |
| 5 | 0 | <1 |
| 6 | 0 | <1 |
| 7 | 0 | <1 |
| 8 | 0 | <1 |

What is claimed is:

1. A process for preparing a polymerizable amino acid compound of the formula:

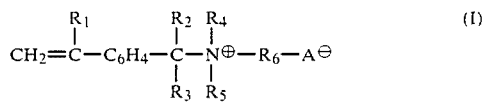

wherein $R_1$, $R_2$ and $R_3$ are each hydrogen or methyl, $R_4$ is $C_1$-$C_{20}$ alkyl optionally substituted with at least one hydroxyl and optionally substituted with —O— or —COO— in the alkyl chain, $R_5$ is hydrogen or $C_1$-$C_{20}$ alkyl optionally substituted with at least one hydroxyl and with or without —O— or —COO— in the alkyl chain, $R_6$ is an alkylene group having not more than 6 carbon atoms and A is —COO— or —SO$_3$—, provided that when $R_4$ is $C_1$-$C_{20}$ alkyl, $R_5$ is not hydrogen which comprises reacting a benzyl halide of the formula:

$$CH_2=\underset{R_1}{C}-C_6H_4-\underset{R_3}{\overset{R_2}{C}}-X \qquad (II)$$

wherein X is chlorine or bromine and $R_1$, $R_2$ and $R_3$ are each as defined above with an amino acid compound of the formula:

$$\underset{R_5}{\overset{R_4}{N}}-R_6-A-H \qquad (III)$$

wherein $R_4$, $R_5$, $R_6$ and A are each defined above under basic conditions at a temperature of 0° to 150° C. in the absence or presence of a solvent.

2. The process according to claim 1, wherein the solvent is alcohol, ethylene glycol monoalkyl ether, dimethylformamide, dimethylsulfoxide or water, or a mixture thereof.

3. The process according to claim 1, wherein the reaction is carried out at a temperature of 0° to 150° C.

4. The process according to claim 1, wherein the reaction is carried out under an atmospheric or elevated pressure.

5. The process according to claim 1, wherein the reaction is carried out for a period of 10 minutes to 48 hours.

* * * * *